United States Patent [19]
Lee

[11] Patent Number: 5,423,330
[45] Date of Patent: Jun. 13, 1995

[54] CAPSULE SUCTION PUNCH INSTRUMENT AND METHOD OF USE

[75] Inventor: William G. Lee, Miami, Fla.

[73] Assignee: The University of Miami, Miami, Fla.

[21] Appl. No.: 29,398

[22] Filed: Mar. 10, 1993

[51] Int. Cl.[6] .......................... A61F 9/00; A61B 17/32
[52] U.S. Cl. .................................. 128/753; 606/166; 606/184
[58] Field of Search ............... 606/166, 184, 167, 172, 606/116, 180, 170; 128/753, 758

[56] References Cited

U.S. PATENT DOCUMENTS

| | | |
|---|---|---|
| 2,919,692 | 1/1960 | Ackermann . |
| 3,074,407 | 1/1963 | Moon et al. . |
| 3,727,602 | 4/1973 | Hyden et al. ......................... 128/753 |
| 3,844,272 | 10/1974 | Banko ................................... 128/753 |
| 3,990,453 | 11/1976 | Douvas et al. . |
| 4,556,059 | 12/1985 | Adamson, Jr. . |
| 4,617,940 | 10/1986 | Wang .................................... 128/753 |
| 4,654,030 | 3/1987 | Moll et al. ............................ 604/165 |
| 4,733,662 | 3/1988 | DeSatnick et al. . |
| 4,796,623 | 1/1989 | Krasner . |
| 4,890,626 | 1/1990 | Wang .................................... 128/752 |
| 4,931,042 | 6/1990 | Holmes et al. ....................... 604/164 |
| 4,958,625 | 9/1990 | Bates et al. ........................... 128/754 |

Primary Examiner—Tamara L. Graysay
Attorney, Agent, or Firm—Cushman, Darby & Cushman

[57] ABSTRACT

A surgical instrument is provided having a tubular body including a distal portion, a proximal portion and a mid portion. A cutting member having a cutting edge is longitudinally received within the tubular body for guided reciprocal movement therein between a cutting position wherein the cutting edge extends from the distal portion and a non-cutting position wherein the cutting edge is retracted within the tubular body. A urging mechanism is also provided within the mid portion of the tubular body for urging the cutting member to the cutting position. A vacuum source is coupled to the cutting member at a proximal end thereof and provides a vacuum directed to the distal portion to hold tissue to be cut. A method of cutting the tissue is also provided.

23 Claims, 16 Drawing Sheets

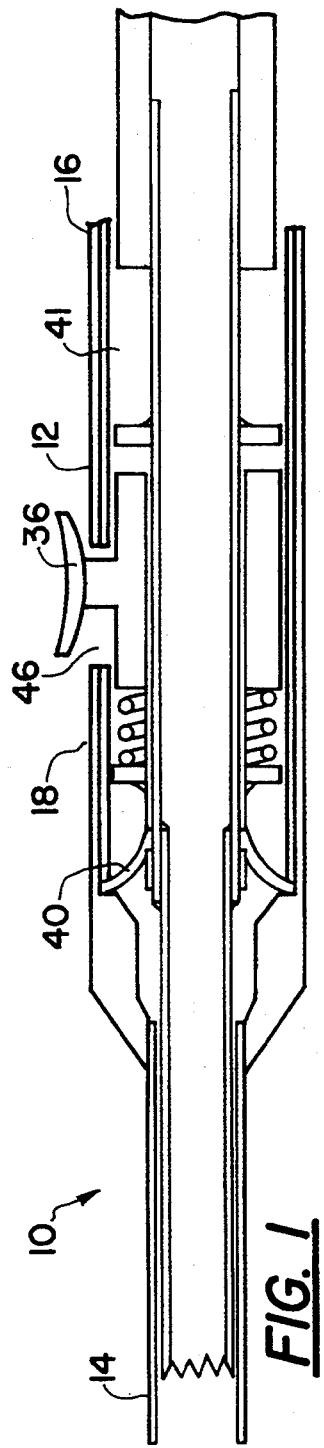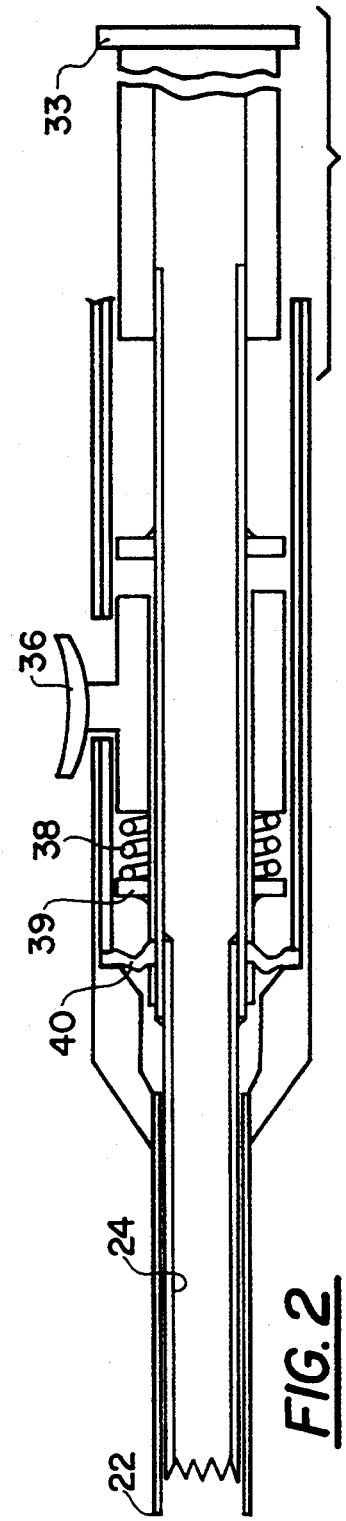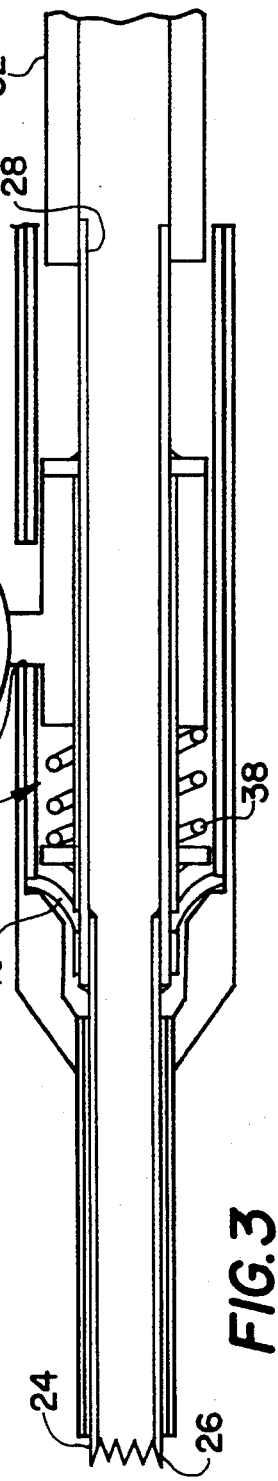

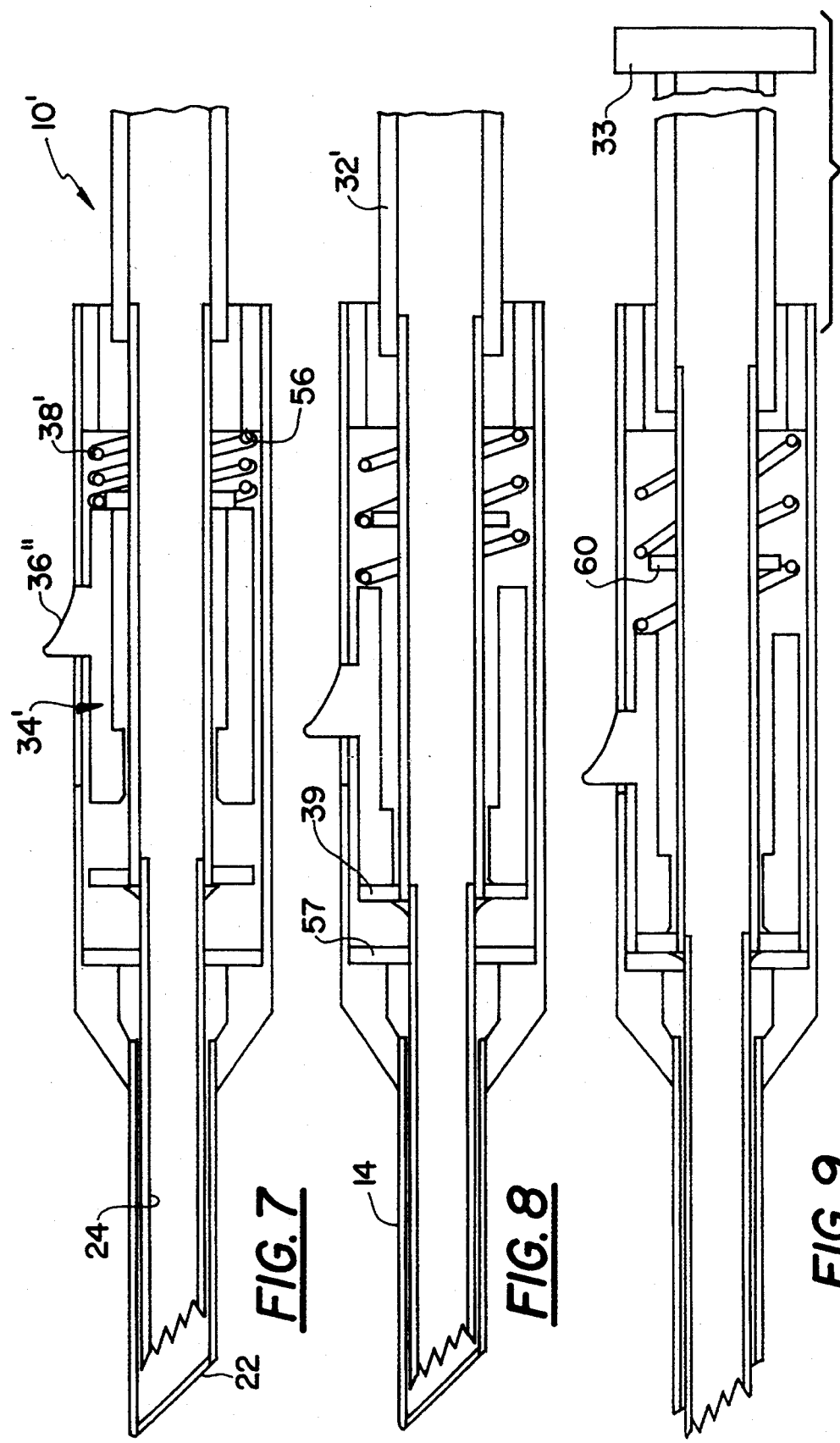

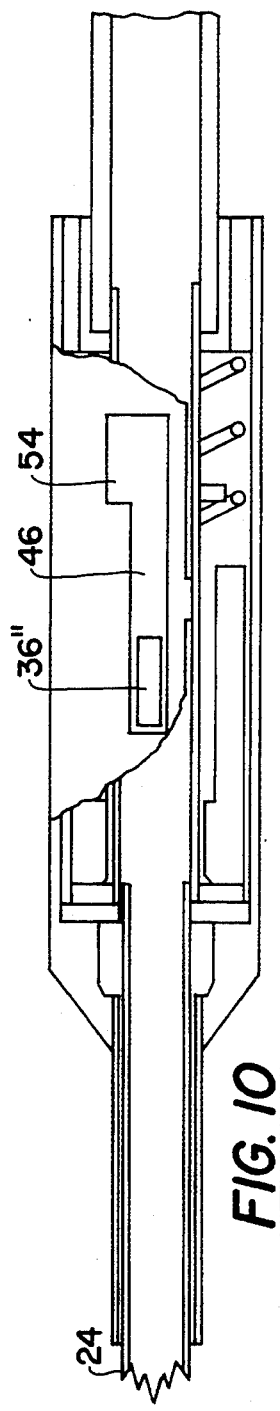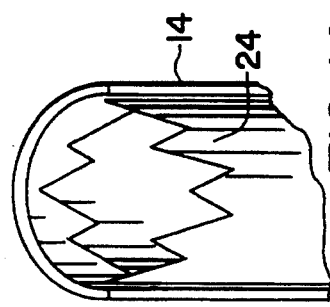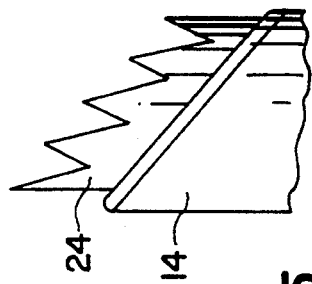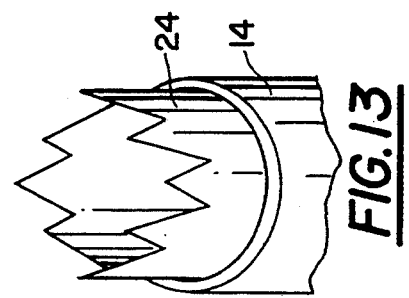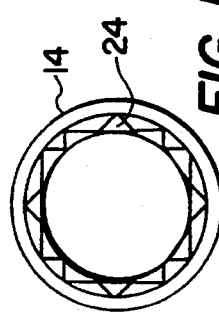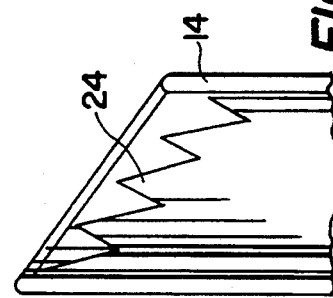

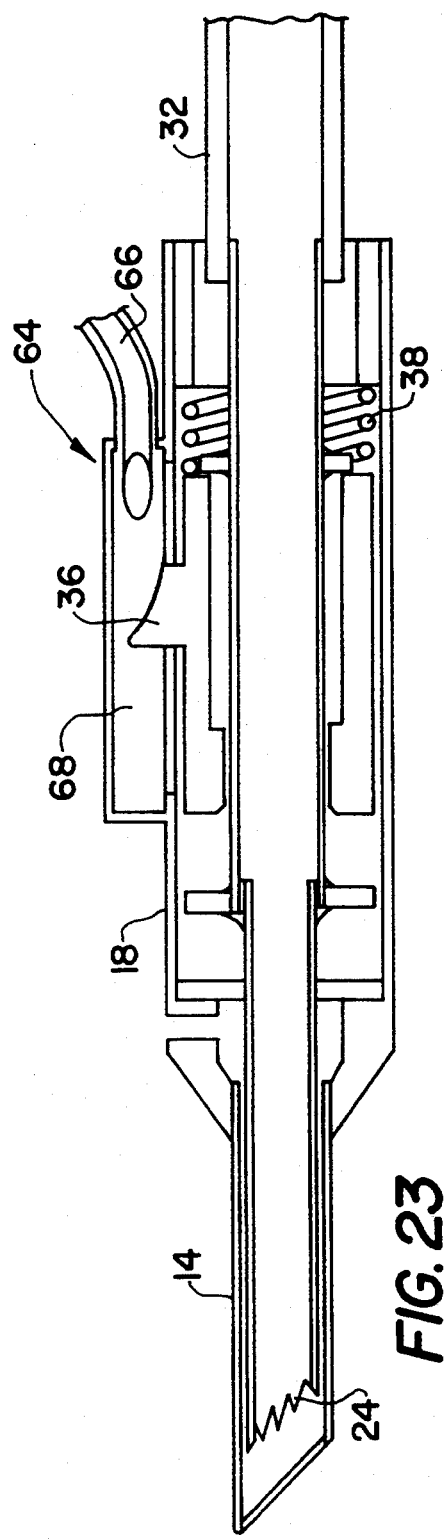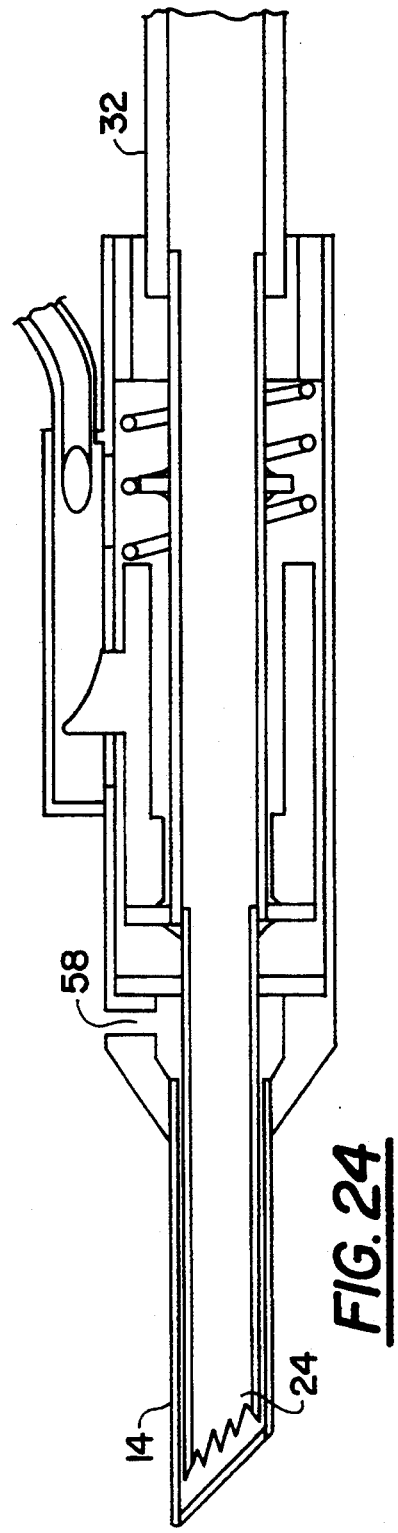

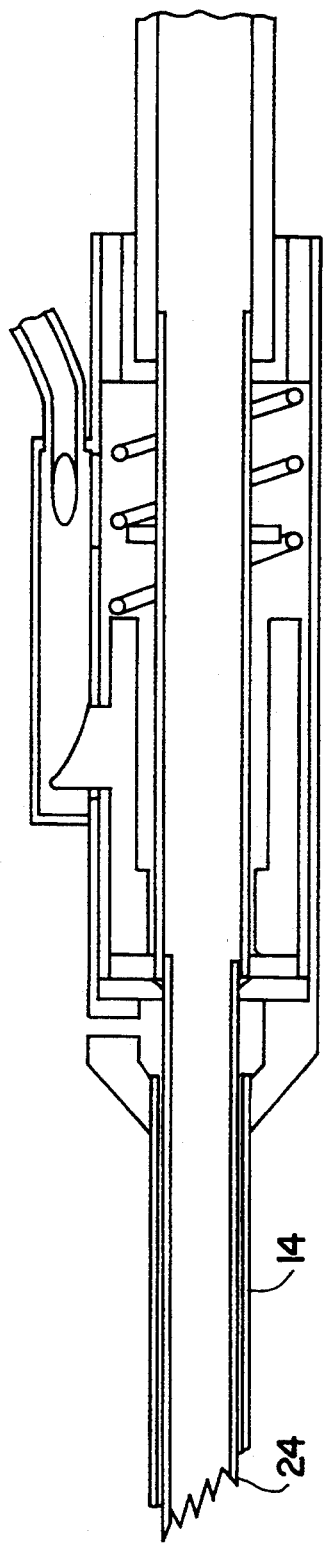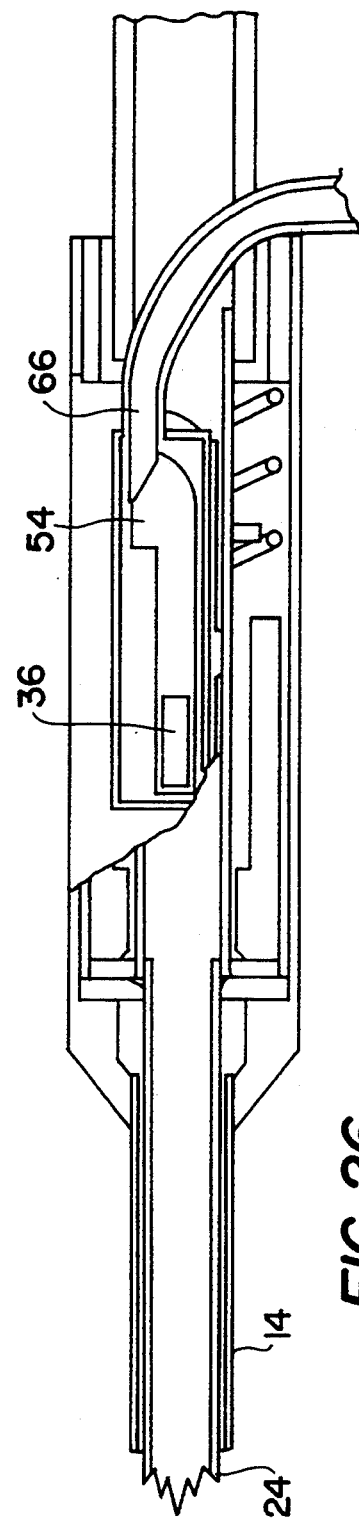
FIG. 25
FIG. 26

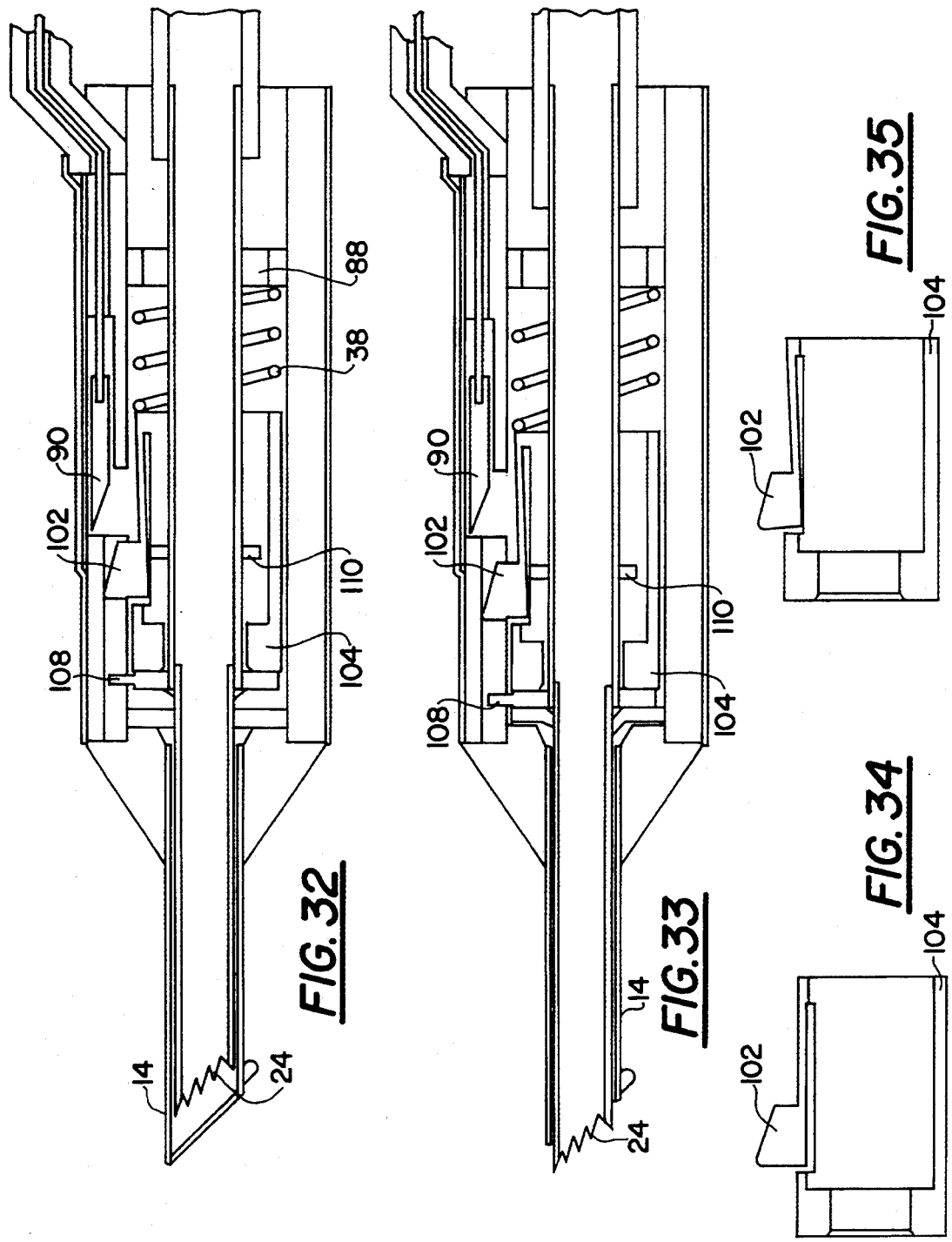

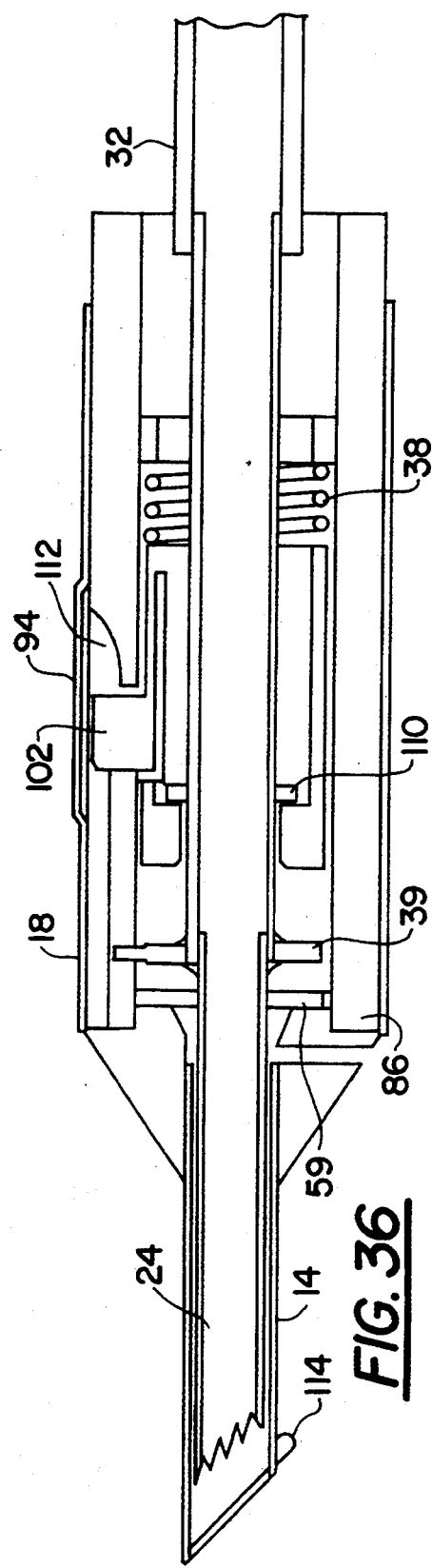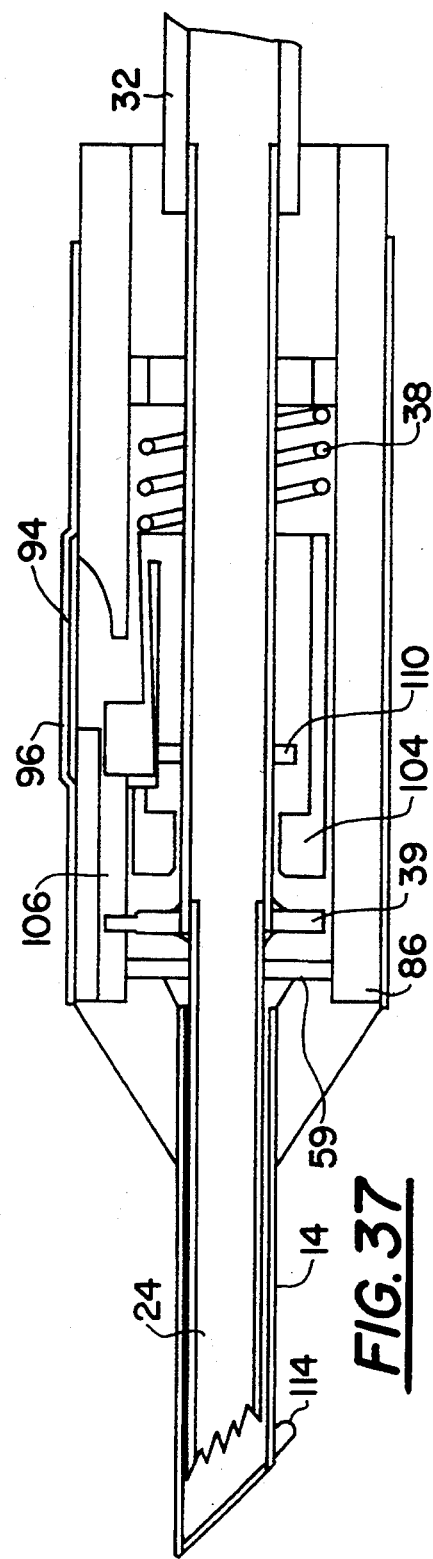

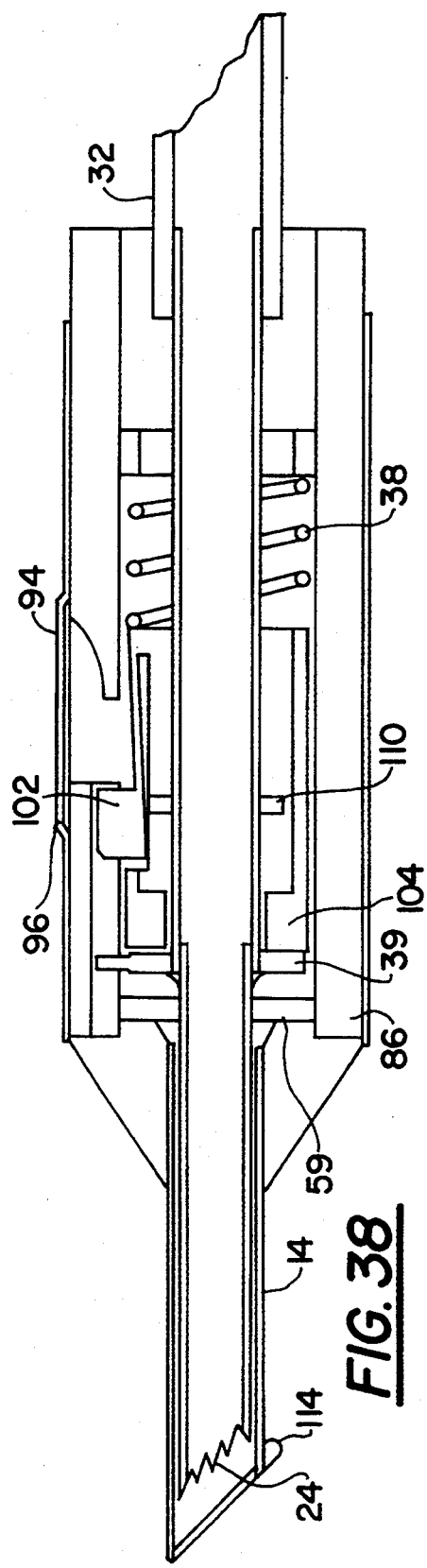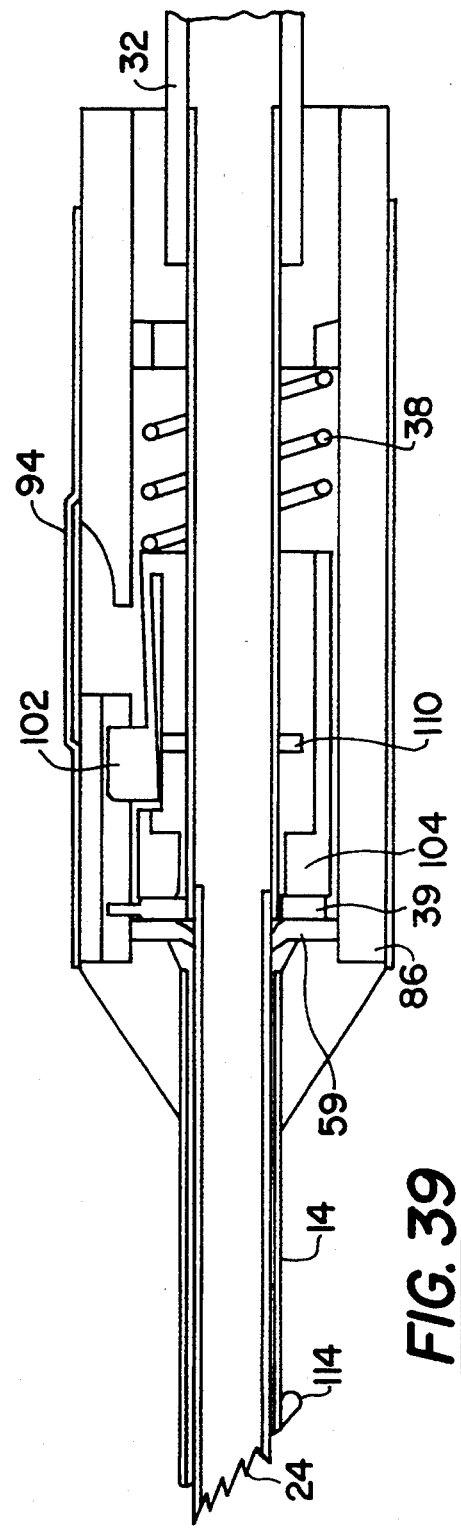

CAPSULE SUCTION PUNCH INSTRUMENT AND METHOD OF USE

BACKGROUND OF THE INVENTION

1. Field of the Invention

This invention relates to an instrument for cutting tissue and, more particularly, to an instrument for creating a hole or flap in the lens capsule of the eye.

2. Description of Related Art

Many surgical procedures require incision of membranes and the like for insertion of instruments. For example, when incising the lens capsule, straight cuts are typically made with cutting instruments having extremely sharp blades and instruments are thereafter inserted to carry out the desired surgical procedure. However, stress concentration occurs at edges of the straight cut when instruments are manipulated in the incision, which may result in tearing of the incision. To eliminate the problems of stress concentration, circular cuts have been proposed. However, the physical nature of tissue being cut often precludes a clean incision, since the tissue may collapse or distort when initial penetration is made with the cutting instrument. Thus, conventional instruments do not facilitate a clean cut since the tissue cannot be properly held during the cutting operation. Further, precise circular cuts cannot be made with conventional instruments due to their slow cutting speeds.

In other surgical procedures, clean cuts are also required to retrieve biopsy specimens or to remove a precise segment of tissue for transplants. For example, in keratoplasty utilizing corneal transplantation, a precise piece of the cornea must be removed.

SUMMARY OF THE INVENTION

An object of the invention is to provide an instrument for cutting the lens capsule which overcomes the problems associated with the conventional instruments by producing an incision which resists tearing.

Another object of the invention is to provide an instrument for cutting the lens capsule which ensures that a tissue specimen will not be inadvertently cut or punched during positioning of the instrument.

A further object of the invention is to provide an instrument which is capable of holding eye tissue during the cutting procedure so as to facilitate a clean cut in the lens capsule.

The foregoing and other objects are realized by providing a surgical suction punch instrument which includes a tubular body having a proximal portion and a distal portion. A cutting member which has a distal cutting edge is longitudinally received within the tubular body for guided reciprocal movement therein between a cutting position wherein the cutting edge projects from the distal portion and a non-cutting position wherein the cutting edge is retracted within the tubular body. An urging mechanism is further provided, preferably within the tubular body, for urging the cutting member toward its cutting position. A vacuum source is coupled to the tubular body and/or the cutting member and provides a vacuum to hold tissue to be cut during the cutting procedure.

Another object of the present invention is the provision of the device of the type described, which is simple in construction, effective in operation and economical to manufacture and maintain.

Other objects, features, and characteristics of the present invention, as well as the methods of operation and functions of the related elements of the structure, and the combination of the parts and economies of manufacture, will become more apparent upon consideration of the following detailed description and the appended claims with reference to the accompanying drawings, all of which form a part of the specification.

BRIEF DESCRIPTION OF THE DRAWING

FIG. 1 is a schematic sectional view of an instrument provided in accordance with the invention, shown with its cutting member in a retracted, non-cutting position;

FIG. 2 is a schematic sectional view of the instrument of FIG. 1, shown with its cutting member in transition from a non-cutting to a cutting position;

FIG. 3 is a schematic sectional view of the instrument of FIG. 1, shown with its cutting member in a cutting position;

FIG. 7 is a schematic sectional view of a second embodiment of the invention, shown with its cutting member in a retracted, non-cutting position;

FIG. 8 is a schematic sectional view of the instrument of FIG. 7, shown with its cutting member in transition from the non-cutting position to the cutting position;

FIG. 9 is a schematic sectional view of the instrument of FIG. 7, shown with its cutting member in the cutting position;

FIG. 10 is a schematic top plan view of the instrument of FIG. 7;

FIG. 11 is an end view of the cutting member disposed within the distal portion of the tubular body of the instrument;

FIG. 12 is a sectional side view of a portion of the cutting member disposed within the distal portion of the tubular body;

FIG. 13 is a perspective view of a portion of the cutting member extending from the distal portion of the tubular body;

FIG. 14 is a partially cutaway perspective view of a portion of the cutting member retracted within the distal portion of the tubular body;

FIG. 15 is a side view of a portion of the cutting member extending from the distal portion of the tubular body;

FIG. 23 is a schematic sectional view of a third embodiment of the invention, shown with its cutting member in a retracted, non-cutting position;

FIG. 24 is a schematic sectional view of the instrument of FIG. 23, shown with its cutting member in transition from the non-cutting position to the cutting position;

FIG. 25 is a schematic sectional view of the instrument of FIG. 23, shown with its cutting member in the cutting position;

FIG. 26 is a schematic top plan view of the instrument of FIG. 23;

FIG. 32 is a schematic sectional view of the instrument of FIG. 30, shown with its spring loaded slide in contact with the thrust plate;

FIG. 33 is a schematic side plan view of the instrument of FIG. 30, shown with its cutting member in the cutting position;

FIG. 34 is a view of a portion of a spring arm of the invention, shown in a relaxed position;

FIG. 35 is a view of the spring arm of FIG. 34, shown in a biased position;

FIG. 36 is a schematic sectional view of a sixth embodiment of the invention, shown with its cutting member in a retracted, non-cutting position;

FIG. 37 is a schematic sectional view of the instrument of FIG. 36, shown with its cutting member in transition from the non-cutting position to a cutting position;

FIG. 38 is a schematic sectional view of the instrument of FIG. 36, shown with its spring loaded slide in contact with the thrust plate;

FIG. 39 is a schematic side plan view of the instrument of FIG. 36, shown with its cutting member in the cutting position;

DETAILED DESCRIPTION OF THE PREFERRED EMBODIMENTS

Figure 4:
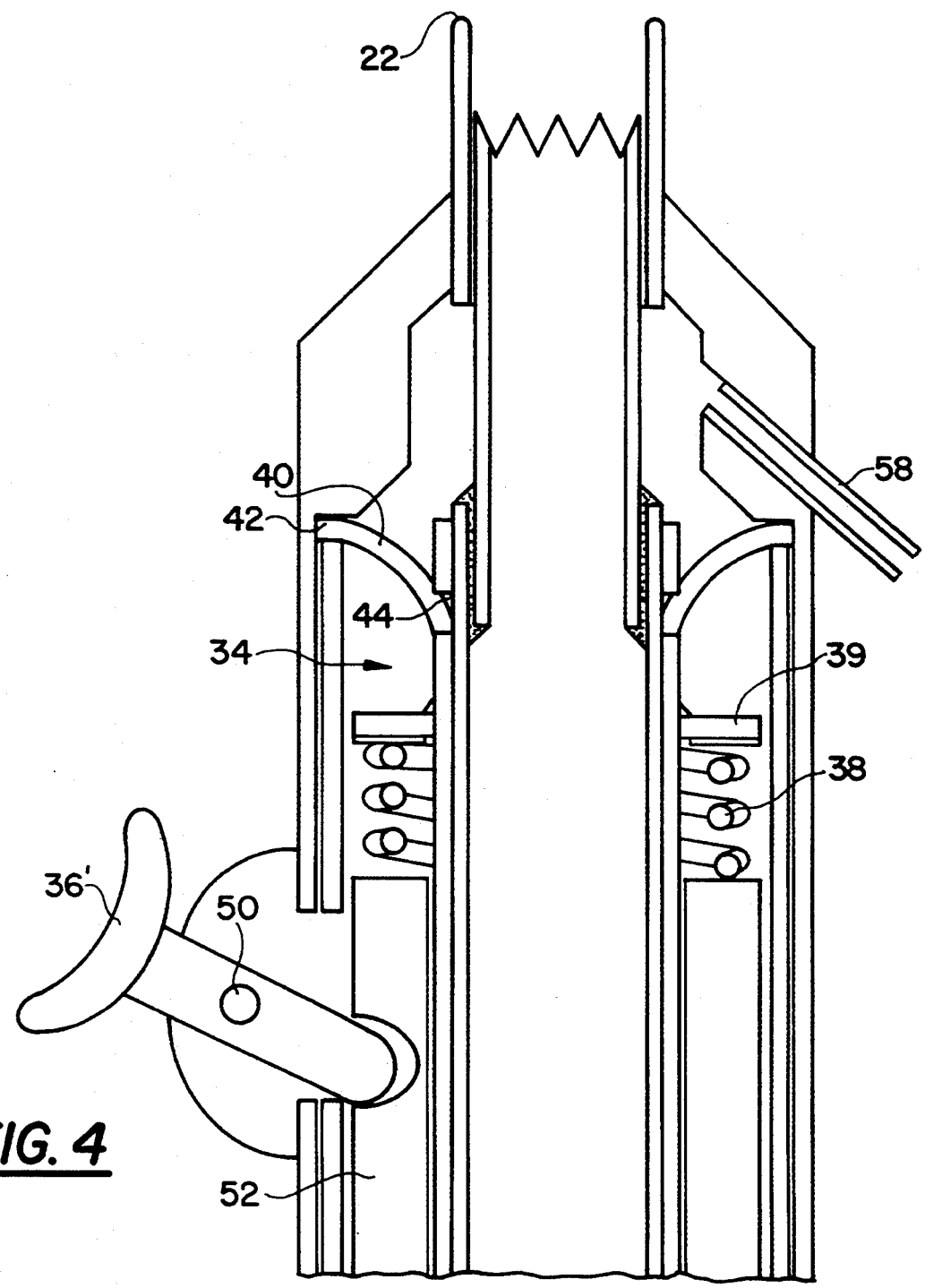
FIG. 4 is an enlarged schematic sectional view of a portion of the instrument showing a pivoted finger slide.

Referring to the drawings, several embodiments of a surgical instrument which embodies of the principles of the present invention, are shown.

Figure 6A:
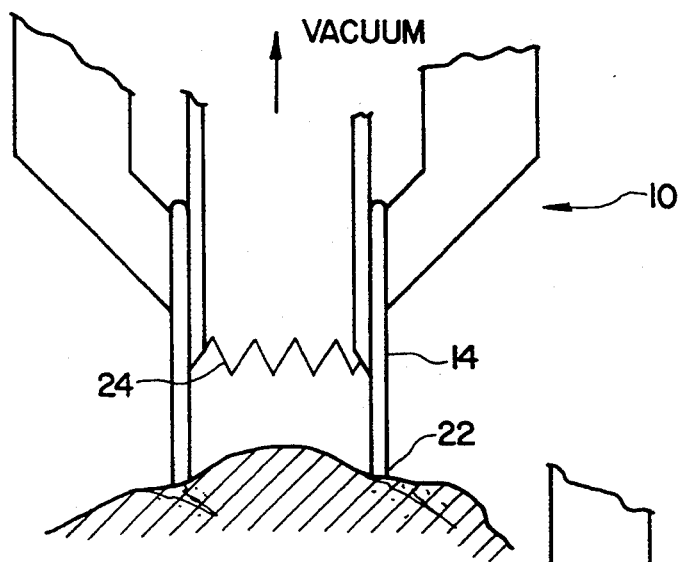
FIG. 6a is a schematic view of the distal portion of the instrument engaging tissue, with a vacuum being exerted on the tissue to hold the tissue prior to cutting.
Figure 6B:
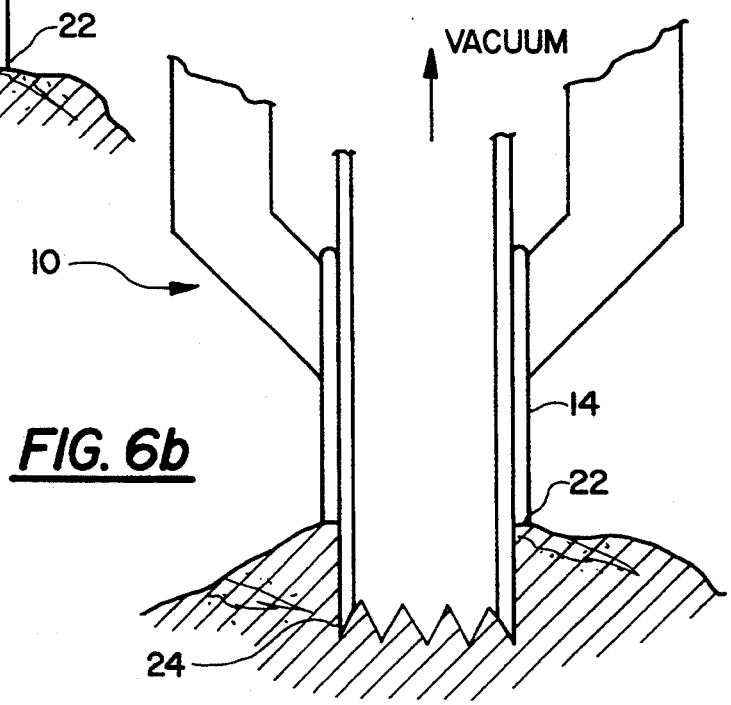
FIG. 6b is a schematic view of the distal portion of the instrument with the cutting member cutting the tissue.
Figure 16:
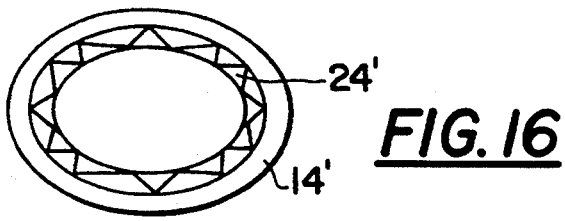
FIG. 16 is an end view of an elliptical cutting member provided in accordance with the invention.
Figure 17:
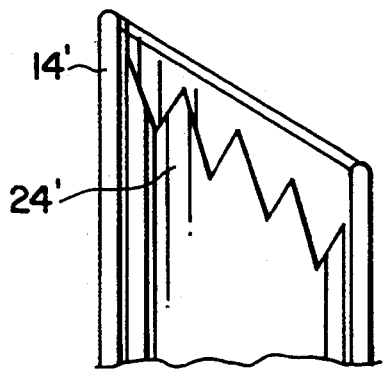
FIG. 17 is a sectional side view of a portion of the elliptical cutting member of FIG. 16, shown disposed within the distal portion of the tubular body.
Figure 18:
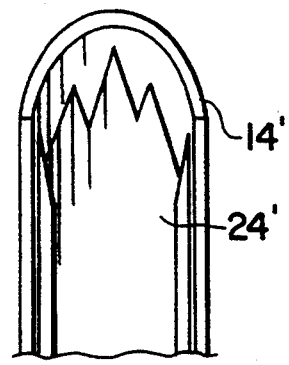
FIG. 18 is a partial top view of the elliptical cutting member of FIG. 16, shown disposed within the distal portion of the tubular body.
Figure 19:
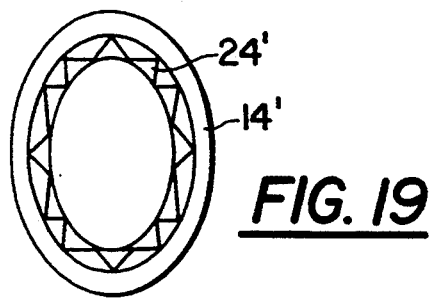
FIG. 19 is an end view of a portion of another elliptical cutting member of the invention.
Figure 20:
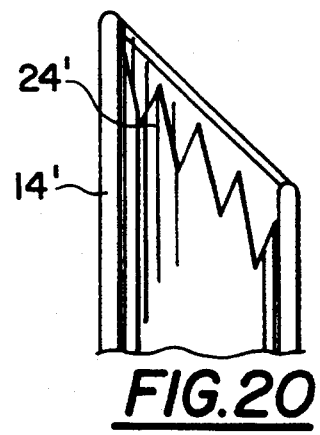
FIG. 20 is a sectional side view of a portion of the elliptical cutting member of FIG. 19, shown disposed within the distal portion of the tubular body.
Figure 21:
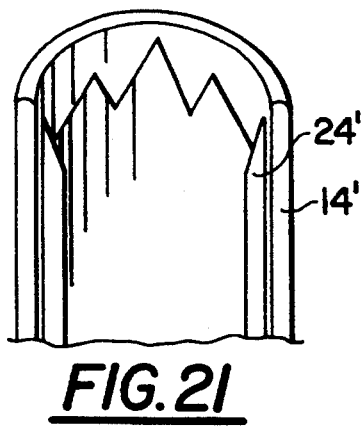
FIG. 21 is a partially cutaway top view of a portion of the elliptical cutting member of FIG. 19, shown disposed within the distal portion of the tubular body.

In general, the instrument of the invention is utilized to hold tissue, such as the lens capsule of the eye, with a vacuum while performing a quick-action cut of the tissue, resulting in a clean circular cut, as shown in FIGS. 6a and 6b. When the eye is incised, the instrument reduces the pressure on the inside of the lens capsule. The instrument permits removal of part of the capsule and lens tissue or creates a flap in the capsule so as to make room for other surgical instruments or implants. Upon completion of the cutting procedure, the instrument may be disposed of, or sterilized for further use. It can be appreciated that the instrument can be used to cut eye tissue other than the lens capsule, such as the cornea, and body tissue other than eye tissue.

With reference to the embodiment of FIG. 1, the instrument 10 includes a tubular body 12 having a distal portion 14, a proximal portion 16 and a mid portion 18. The distal portion of the tubular body extends from the mid portion and may have a diameter less than that of the mid portion, as shown. In the embodiment of FIG. 1, the edge 22 of the distal portion 14 is in a plane perpendicular to the longitudinal axis of tubular body 12 and is blunt. The shape of edge 22 is chosen to match the contour of the tissue to be cut. Thus, it can be appreciated that end or edge 22 of the distal portion may be angled, as shown in FIG. 7, to properly hold during cutting tissue that is curved.

Figure 5A:
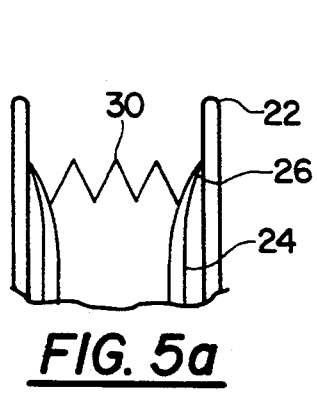
FIG. 5a is an enlarged view of a distal end of an instrument in accordance with the invention showing a cutting member having a flared blade in a retracted position.
Figure 5B:
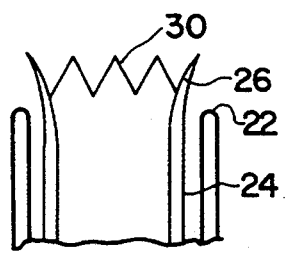
FIG. 5b is an enlarged view of the distal end of the instrument showing the cutting member with a flared blade in an extended position.

Disposed centrally within the tubular body 12 is a cutting member 24 which is mounted for guided reciprocal movement within the tubular body. The cutting member 24 is of hollow tubular construction having distal 26 and proximal 28 ends. The distal end 26 of the cutting member includes a cutting edge or blade 30. As shown in FIGS. 5a, 5b, and 11–21, the cutting blade 30 may have a variety of configurations, but each is preferably peripherally continuous, serrated and adapted to make a circular or oval hole. FIGS. 5a and 5b show a cutting blade 30 having a flared end. The flared end is provided so there is no gap between the inner side of the distal end 14 and the cutting member 24, while permitting infusion or vacuum to flow through the space between the grooves of the cutting member. The flared end also acts as a spring member to hold the cutting member 24 from sliding until the shoulder means or thrust plate 39 thrusts it forward, as will become more apparent below.

In the illustrated embodiment, the proximal end 28 of the cutting member 24 is coupled to a flexible tube 32 which is connected to a vacuum source 33, as will become more apparent below.

To provide a quick-acting cutting instrument, an urging mechanism, generally indicated at 34, is provided which is coupled to the cutting member 24 so as to urge the cutting member toward a cutting position (FIG. 3) from a non-cutting position (FIG. 1). Urging mechanism 34 spring loads the cutting member for selective release to cut tissue. Thus, in one embodiment, the urging mechanism 34 includes a finger slide 36 disposed about the cutting member 24. A spring member 38 is disposed forward of the finger slide 36, between the finger slide and a thrust plate 39. The thrust plate 39 is coupled to the periphery of the cutting member 24.

The urging mechanism further includes a diaphragm member 40 having an outer periphery 42 and an inner periphery 44. The outer periphery 42 of the diaphragm member 40 is sealingly coupled with the mid portion 18 of the tubular body. The inner periphery of the diaphragm member is sealingly coupled with the cutting member 24. The diaphragm member 40 is made of resilient material so that when it is moved from a first rest state (FIG. 1) through a cocked or loaded state (FIG. 2) to a second rest state (FIG. 3), the diaphragm member moves the cutting member from the non-cutting position to the cutting position, as will become apparent below. The diaphragm member 40 further ensures that a vacuum is confined to the cutter and to the distal portion 14 to assist in holding, severing and capturing part of the capsule or other tissue to be severed.

As shown in FIG. 1, when the finger slide 36 is disposed at the rear of channel 46, the distal end 26 of the cutting member 24 is disposed within the tubular distal portion 14 of the tubular body, with the diaphragm member in a rest state.

FIG. 2 shows the diaphragm member 40 in a "cocked" state just prior to release. Thus, the finger slide 36 is moved forward with spring 38 compressed. Diaphragm member 40 is deformed which moves the cutting member 24 slightly forward.

FIG. 3 shows the finger slide 36 moved all the way to the forward end of channel 46. The spring member 38 forces the thrust plate 39 forward which causes the diaphragm member 40 to spring forward to a rest, released state, thus moving the cutting member to an extended cutting position. In such a position, the distal end 26 of the cutting member projects from the distal portion 14 of the tubular body so as to protrude from blunt end 22. A stop 48 defines an end of channel 46 to limit movement of the finger slide 36 and thus, movement of the cutting member 24. The use of the diaphragm member 40 to actuate the cutting member increases the speed at which tissue can be cut by the instrument 10. The serrated distal end 26 of the cutting member facilitates holding, piercing and penetrating of tissue, as shown in FIGS. 6a, 6b. To prevent air bubbles from entering the body organ being cut, the cutting member 24 may be filled with a fluid such as saline.

As is apparent from the foregoing, the invention provides an instrument which enables tissue, whether hard or soft, to be effectively held and cut, even at substantial depths, without affecting other adjacent areas.

FIG. 4 shows a variation of the finger slide 36'. As shown, the slide 36 includes a pivot 50 which, when rotated, moves sliding member 52.

FIG. 4 also shows an infusion port 58 connected to the mid portion 18 of the tubular body and communicating with the space between the inner periphery of the distal portion 14 of the tubular body and the outer periphery of the cutting member 24 to provide infusion of materials required during the tissue extraction procedure. The infusion port may also be used to release the vacuum.

FIGS. 7-10 illustrate a second embodiment of the present invention. The second embodiment is substantially similar to the first embodiment; however, the urging mechanism 34 has been modified. As shown in FIG. 10, the finger slide 36" is disposed within channel 46. The channel 46 has a stop 48 at one end thereof and a latch 54 at the opposite end thereof. When the cutting member 24 is retracted within the tubular body into a non-cutting position, the finger slide 36" is engaged with latch 54 to prevent movement of the cutting member. As shown in FIG. 7, the spring member 38' is disposed rearwardly of the finger slide 36", between the finger slide and surface 56. In the non-cutting position, the cutting member 24 is retracted within the tubular body with the spring member 38' compressed. As the finger slide 36" is released from latch 54 (by rotation), spring member 38' is free to expand, moving the finger slide 36" forward. The finger slide 36" contacts the thrust plate 39 which moves the cutting member 24 forward so as to extend from the distal portion 14 of the tubular body, as shown in FIG. 9. A stop 57 is defined by or mounted to the tubular body 12 to engage the thrust plate 39 to limit the movement of the cutting member 24.

A retracting member 60 is provided on the proximal portion of the cutting member 24. Engagement of the finger slide and the retracting member retracts the cutting member during "cocking" of the spring.

Referring to FIGS. 23-26, a third embodiment of the present invention is shown. The third embodiment is substantially similar to the second embodiment; however, a triggering mechanism, generally indicated at 64, is employed. It has been found that in using the spring loaded finger slide, the surgeon may move his hand when he pushes the slide 36, which may damage adjacent tissue. Therefore, a remote electric, mechanic or pneumatic tripping device 66 is employed whereby the user's hand can be kept as steady as possible. The tripping device is disposed in a channel 68. As shown in FIG. 26, the tripping device 66 is remotely actuated to disengage the slide 36 from latch 54.

Figure 27:
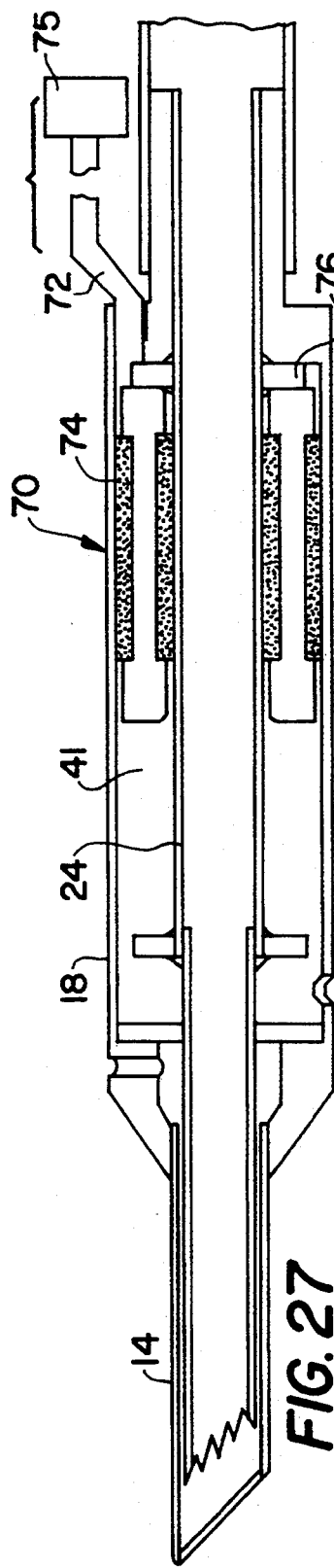
FIG. 27 is a schematic sectional view of a fourth embodiment of the invention, shown with its cutting member in a retracted, non-cutting position.
Figure 28:
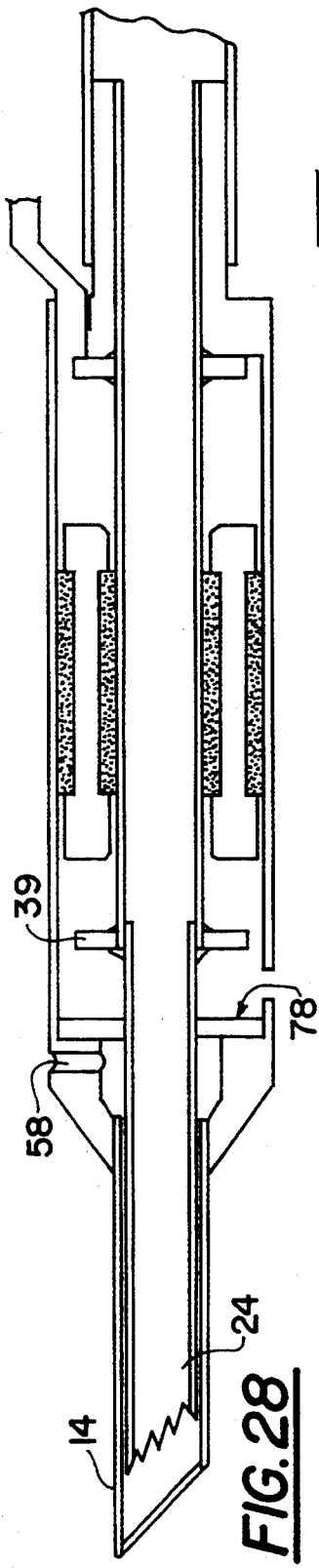
FIG. 28 is a schematic sectional view of the instrument of FIG. 27, shown with its cutting member in transition from the non-cutting position to a cutting position.
Figure 29:
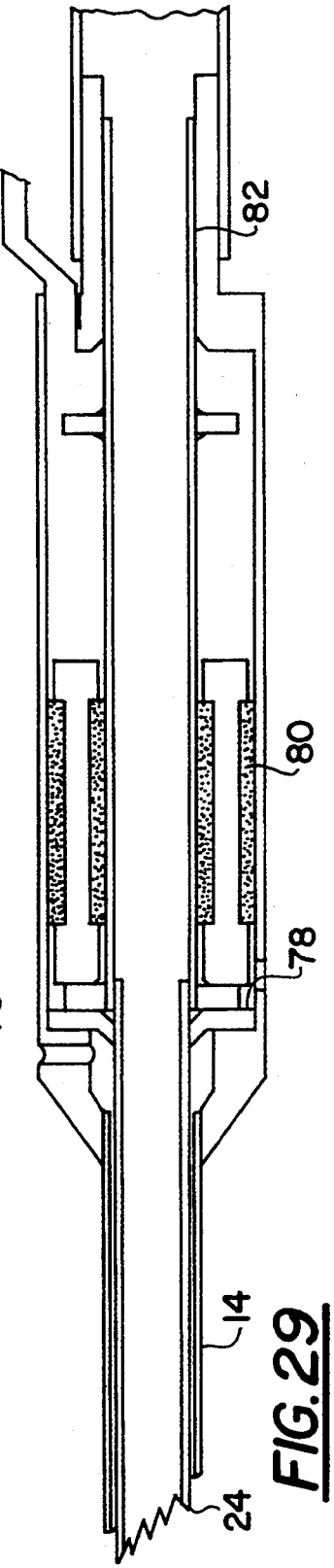
FIG. 29 is a schematic sectional view of the instrument of FIG. 27, shown with its cutting member in the cutting position.
Figures 30, 31:
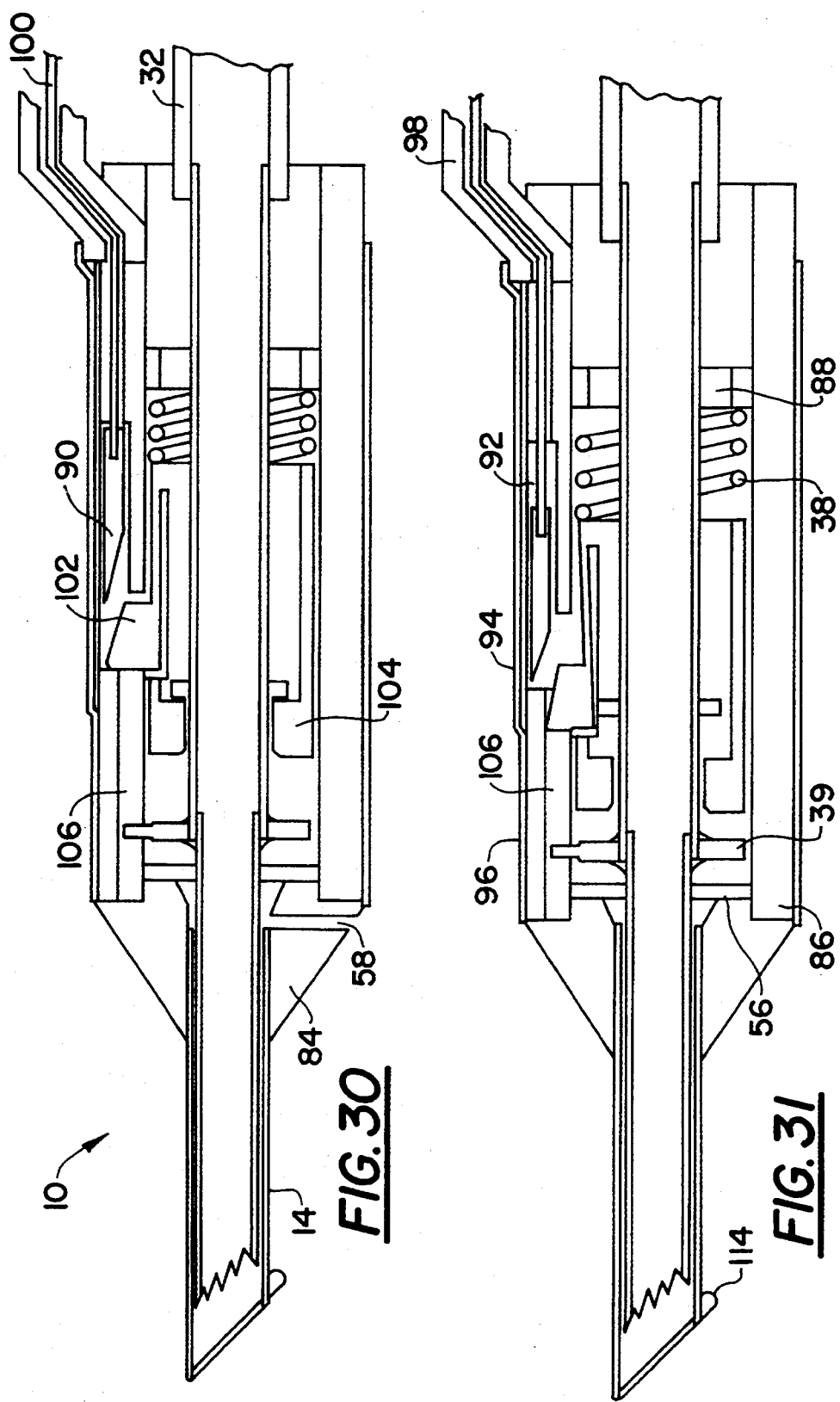
FIG. 30 is a schematic sectional view of a fifth embodiment of the invention, shown with its cutting member in a non-cutting position.
FIG. 31 is a schematic sectional view of the instrument of FIG. 30, shown with its cutting member in transition from the non-cutting position to the cutting position.
Figure 40:
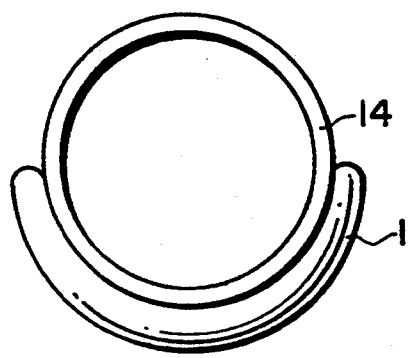
FIG. 40 is an end view of the distal portion of the tubular body showing a tissue manipulator disposed thereon.
Figure 41:
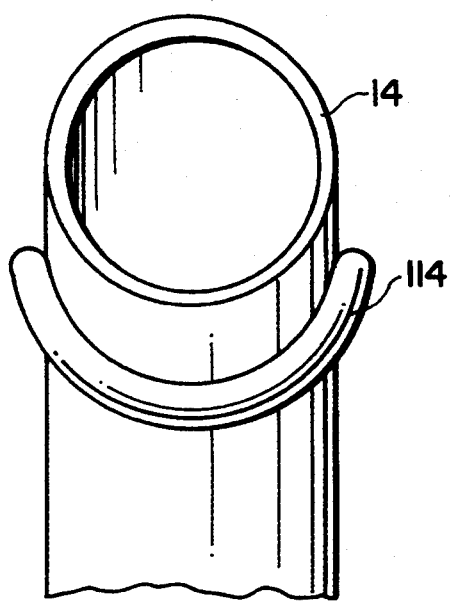
FIG. 41 is a perspective view of a portion of the distal portion of the tubular body having a partial tissue manipulator.
Figure 42:
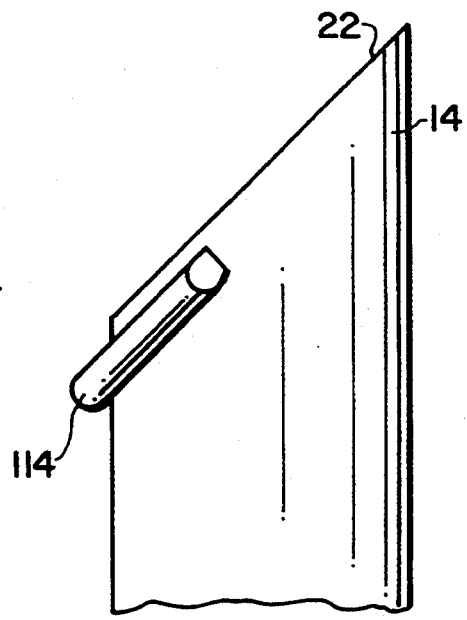
FIG. 42 is a side view of a portion of an angled distal portion of the tubular body having a partial tissue manipulator.
Figure 43:
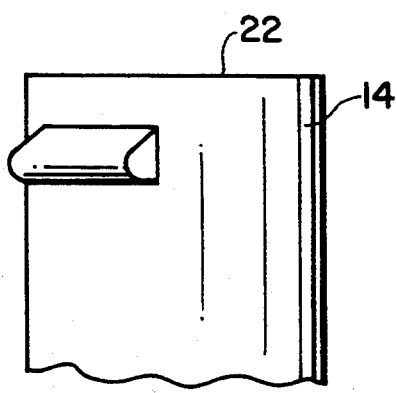
FIG. 43 is a side view of a portion of the distal portion of the tubular body having a partial tissue manipulator.

FIGS. 27-29 disclose a fourth embodiment of the invention having a pneumatically controlled trigger device 70 that is easy to use and simple to manufacture. As shown, a port 72 communicates with the interior of the mid portion 18 of the tubular body so as to move slide member 74, disposed about cutting member 24. A pump/vacuum 75 is used to move the slide member forward into the cutting position or backward to move the cutting member 24 into the retracted position. When the slide member 74 moves forward, it contacts thrust plate 39 which moves the cutting member 24 forward to extend from end 22. A diaphragm seal 78 limits the forward movement of cutting member 24. Stop 76 is provided to limit rearward movement of the slide member 74.

At the forward end of the mid portion 18, the diaphragm seal 78 is provided. When the sliding member 74 contacts the thrust plate 39, the thrust plate is moved forward to contact the diaphragm seal 78. The diaphragm seal ensures that the vacuum is only provided within the interior of the cutting member and cannot be released into chamber 41 of mid portion 18 of the tubular body. Seals 80 and 82 are also provided about the sliding member 74 and about the proximal end of the cutting member 24 so as to prevent loss of vacuum.

FIGS. 24 and 28, in particular, show an infusion port 58 communicating with a chamber between the outer periphery of the cutting member 24 and the inner periphery of the distal portion 14 of the tubular body. This port 58 can be used to release the vacuum that is provided in the flexible tube 32. The port can also be used to provide infusion. Of course, the port must be sealed when vacuum is applied.

FIGS. 30–35 illustrate a fifth embodiment of the present invention which is substantially similar to the third embodiment of the invention; however, the fifth embodiment has a modified remote actuating mechanism. As shown, the mid portion 18 of the tubular body includes a hub 84 which is coupled to the distal portion 14 of the tubular body. The other end of the hub is coupled to a cavity tube 86. The cavity tube 86 is attached to a spring retainer 88.

A wedge trip slide 90 is provided which slides in cavity 92 of cavity tube 86. The wedge trip slide 90 is preferably covered by a film cover plate 94 and held in place, preferably by a tape 96 attached to the cavity tube and a trip wire guard 98. The wedge trip slide 90 is attached to a trip wire 100. The wedge trip slide, when pushed against spring arm 102 of the spring loaded slide 104, unlatches slide 104 so as to slide along groove 106. The spring loaded slide 104 is pushed by the spring member 38. The spring loaded slide 104 makes contact with the thrust plate 39, which moves the cutting member 24 forward. The spring arm 102 is shown in its relaxed state in FIG. 34, whereas FIG. 35 shows the spring arm 102 in a biased state.

An anti-rotation tab or protrusion 108 extends from thrust plate 39 into groove 106. This prevents rotation of the cutting member 24 in operation.

A seal 59 is provided between the cavity tube and the cutting member. The seal 59 also acts as a shock absorber when contacted by the thrust plate 39.

A retractor 110 is provided about the cutting member 24 so as to permit the cutting member to be retracted within tubular body 12 after cutting the desired tissue.

FIGS. 36–39 illustrate a sixth embodiment of the present invention. The sixth embodiment is similar to the fifth embodiment; however, manual, instead of remote, actuation is required. As shown, a notch 112 is defined in the mid portion 18 near the spring arm 102. The notch 112 is covered by a flexible film cover plate 94 which is held in place by tape 96 attached to the cavity tube 86. When the cover plate 94 is manually depressed, spring arm 102 is moved downward. Spring member 38 forces the spring loaded slide 104 to move along the mid portion 18 of the tubular body. The slide 104 slides along groove 106. The spring loaded slide 104 is pushed by the spring member 38 and contacts the trust plate 39, which moves the cutting member 24 forward so as to extend from the distal end of the tubular body, thereby defining the cutting configuration of the instrument. As in the previous embodiment, seal 59 acts as a stop or shock absorber when contacted by thrust plate 39.

Figure 44:
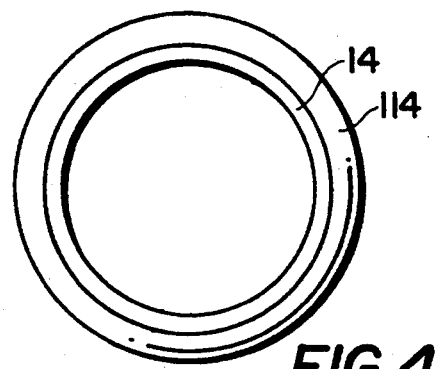
FIG. 44 is an end view of the distal portion of the tubular body having a complete tissue manipulator.
Figure 45:
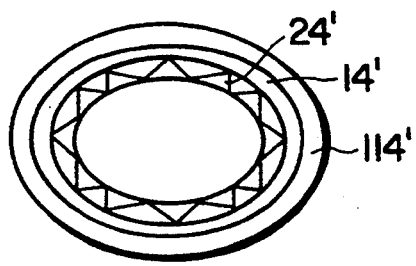
FIG. 45 is an end view of an elliptical distal portion of the tubular body having a complete tissue manipulator.
Figure 46:
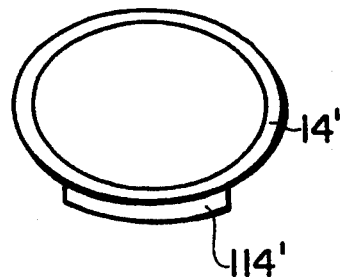
FIG. 46 is an end view of an elliptical distal portion having a partial tissue manipulator.

As shown in FIGS. 40–46, a tissue manipulator 114 is preferably provided on the periphery of the distal portion 14 near end 22. As shown in FIGS. 40–43, the manipulator 114 may be partially disposed about distal portion 14. However, as shown in FIGS. 44 and 45, the manipulator 114 may be disposed about the entire periphery of the distal portion 14 of the tubular body. The tissue manipulator or retracting means 114 is used to retract the iris during the tissue extraction or flap creation procedure. The tissue manipulator can be either sharp or blunt.

Figure 47:
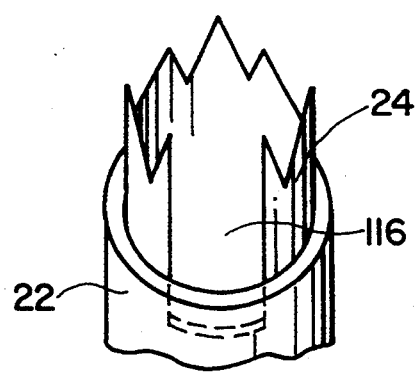
FIG. 47 is a perspective view of a another embodiment of a portion of the cutting member extending from the distal portion of the tubular body for creating a flap in tissue.
Figure 48:
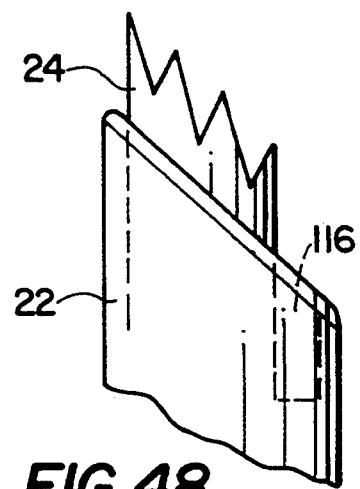
FIG. 48 is a side view of the cutting member of FIG. 47.

Instead of creating a circular incision in the capsule or other tissue, it may be preferable to leave the tissue connected to surrounding tissue at the incision site. Therefore, in accordance with a further aspect of the invention the cutting member 24 may be used to cut a flap in tissue. Referring to FIGS. 47 and 48, the cutting member has been modified to create a flap. As shown, the cutting member includes a cut-out 116. Thus, tissue will not be cut at the cut-out, thereby creating the flap.

Figure 22:
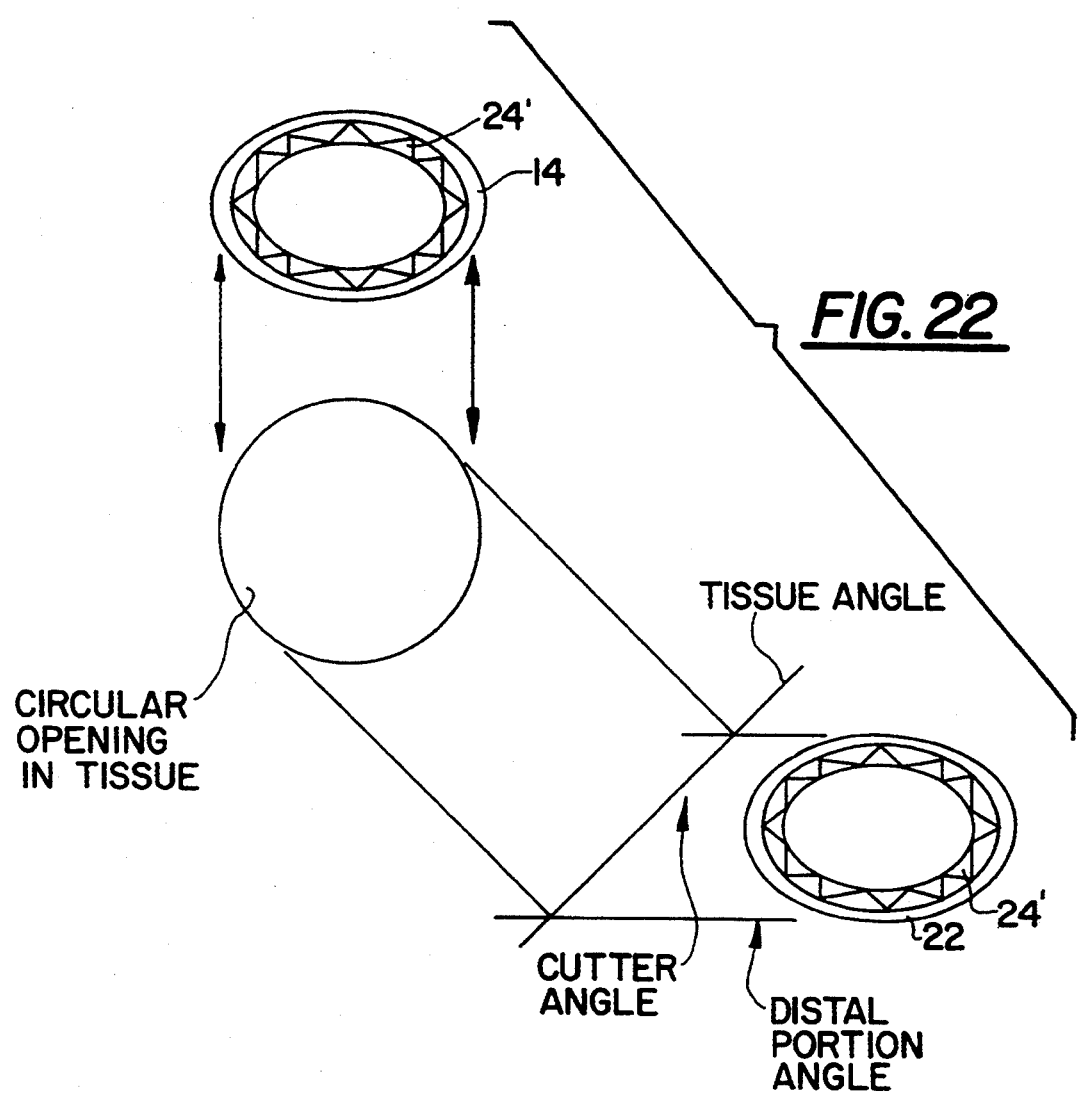
FIG. 22 is a schematic view showing an elliptical cutting member cutting a circular hole.

In accordance with a further feature of the invention, angular cutting members (FIGS. 11–15) may be used to cut elliptical holes in tissue. In addition, elliptical cutting members 24' are provided in accordance witch the invention and are shown in FIGS. 16–22, 45 and 46. FIG. 22 illustrates how an elliptical cutter can be used to cut a circular hole in accordance with the invention.

Thus, it can be appreciated that the invention provides increased assurance that tissue specimens will not be cut or punched and incisions not made during positioning of the instrument. The invention provides a vacuum connected to the flexible tube 32 to retain tissue prior to severing (FIG. 6a). By the particular cooperation between the cutting member 24 and end 22 of the distal portion 14 of the tubular body, tissue is retained in position by the blunt end 22 while the cutting member 24 is in position ready to be released and quickly cut the tissue, without tearing.

While the invention has been described in connection with what is presently considered to be the most practical and preferred embodiments, it is to be understood that the invention is not limited to the disclosed embodiments but, on the contrary, is intended to cover various modifications and equivalent arrangements included within the spirit and scope of the appended claims.

What is claimed is:

1. A surgical instrument comprising:

a tubular body having a distal portion and a proximal portion;

an elongated tubular cutting member having a cutting edge, said cutting member being constructed and arranged with respect to said tubular body so as to be longitudinally received within said tubular body for guided longitudinal reciprocal movement therein between a cutting position wherein said cutting edge projects from said distal portion and a non-cutting position wherein said cutting edge is retracted within the tubular body;

means for selectively urging said cutting member and thus said cutting edge toward said cutting position; and a vacuum source coupled to at least one of said tubular body and said cutting member for generating a vacuum therein, said vacuum source being constructed and arranged with respect to one of said tubular body and said cutting member so as to hold tissue to be cut.

2. The surgical instrument as claimed in claim 1, wherein said cutting member includes a distal end, a proximal end and a passage therethrough, said distal end including said cutting edge, said proximal end being coupled to said vacuum source.

3. The surgical instrument as claimed in claim 1, wherein said distal portion of said tubular body terminates distally in a blunt end and said cutting edge extends beyond said blunt end when said cutting member is disposed in said cutting position.

4. The surgical instrument as claimed in claim 1, wherein said means for selectively urging comprises:
a diaphragm member having an outer periphery and inner periphery, said outer periphery of said diaphragm member being sealingly coupled to said tubular body, said inner periphery of said diaphragm member being sealingly coupled to said cutting member, said diaphragm member being resilient and being in a rest state when said cutting member is disposed in said non-cutting position; and
an actuating element slidably disposed within said tubular body and coupled to said cutting member, movement of said actuating element moves said cutting member so as to move said diaphragm member from said rest state through a cocked or loaded state whereafter the diaphragm member springs said cutting member forward into said cutting position.

5. The surgical instrument as claimed in claim 4, wherein said means for selectively urging further comprises a spring member coupled to said actuating element so as to make the actuating element resilient.

6. The surgical instrument as claimed in claim 4, wherein the cutting member includes a thrust plate disposed on a periphery thereof, said spring member being engaged with said thrust plate and said actuating element.

7. The surgical instrument as claimed in claim 4, wherein said tubular body includes stops to limit movement of said cutting member.

8. The surgical instrument as claimed in claim 4, wherein said actuating element is a finger slide slidably disposed in a channel defined in said tubular body.

9. The surgical instrument as claimed in claim 1, wherein said means for selectively urging comprises:
a spring member;
an actuating element slidably disposed within said tubular body and coupled to said spring member, said actuating element being urged toward the distal portion of the tubular body by said spring member; and
means for holding said actuating element against the urging force of said spring member,
said actuating element being constructed and arranged with respect to said cutting member such that release of said actuating element from said holding means permits said actuating element to move due to urging by said spring, said actuating element thereby moving said cutting member from said non-cutting position to said cutting position.

10. The surgical instrument as claimed in claim 9, further comprising a seal for sealing a gap between an inner periphery of said tubular body and an outer periphery of said cutting member.

11. The surgical instrument as claimed in claim 9, wherein said tubular body includes a stop surface, said spring member being disposed between said stop surface and said actuating member, said cutting member further including a thrust plate extending from a periphery thereof and forward of said actuating element, said spring member forcing said actuating element to contact said thrust plate to move the cutting member to said cutting position.

12. The surgical instrument as claimed in claim 9, wherein said tubular body includes stops to limit movement of said cutting member.

13. The surgical instrument as claimed in claim 9, wherein said actuating element is a finger slide slidably disposed in a channel defined in said tubular body.

14. The surgical instrument as claimed in claim 1, wherein said means for selectively moving comprises:
means defining shoulders in a surface of said cutting member;
an actuating element constructed and arranged with respect to said tubular body so as to be slidably disposed within said tubular body, said actuating element being constructed and arranged with respect to said cutting member and movable from a first position where said cutting member is in said non-cutting position to a second position where said cutting member is in said cutting position;
means for moving said actuating element to one of said first and second positions so that said actuating element contacts one of said shoulders to move said cutting member to one of said cutting and non-cutting position.

15. The surgical instrument as claimed in claim 14, wherein said moving means includes a vacuum and pressure source cooperating with said actuating element.

16. The surgical instrument as claimed in claim 15, wherein said actuating element is disposed between first and second shoulder means, pressure from said pressure source moving said actuating element to contact said first shoulder means to move said cutting member to said cutting position, vacuum from said vacuum source moving said actuating element to contact said second shoulder means to move said cutting member from said cutting position to said non-cutting position.

17. A surgical instrument comprising
a tubular body having a distal portion and a proximal portion;
a cutting member having a cutting edge, said cutting member being longitudinally received within said tubular body and being constructed and arranged with respect to said tubular body for guided reciprocal movement therein between a cutting position wherein said cutting edge projects from said distal portion and a non-cutting position wherein said cutting edge is retracted within the tubular body;
means for selectively urging said cutting member and thus said cutting edge toward said cutting position; and
a vacuum source coupled to at least one of said tubular body and said cutting member for generating a vacuum therein, said vacuum source being constructed and arranged with respect to one of said tubular body and said cutting member so as to hold tissue to be cut,
said means for selectively urging comprising:
means defining a shoulder in a surface of said cutting member;

a spring member;

an actuating element constructed and arranged with respect to said tubular body so as to be slidably disposed within said tubular body and movable from a first position wherein said cutting member is in said non-cutting position to a second position wherein said cutting member is in said cutting position, said spring member being coupled to said actuating element so as to urge said actuating element toward the second position; and means for holding said actuating element against the urging force of said spring member, whereby release of said actuating element from said holding means permits said actuating element to move due to urging by said spring forcing said actuating element into contact with said shoulder means, thereby moving said cutting member to said cutting position, said actuating element including a slide member having a spring arm, said tubular body having surfaces defining a notch portion, said spring arm being in a first, relaxed position when disposed in said notch portion to retain said cutting member in said first, non-cutting position, movement of said spring arm from said first position to a second, biased position permits said spring member to force said slide member to contact said plate element and move said cutting member from said first, non-cutting position to said second, cutting position.

18. The surgical instrument as claimed in claim 17, wherein said tubular body includes stops to limit travel of said cutting member.

19. The surgical instrument as claimed in claim 17, further comprising a remote tripping device cooperating with said actuating element to remotely move said actuating element from said first position to said second position.

20. The surgical instrument as claimed in claim 17, wherein said tubular body includes a groove, said spring arm sliding in said groove when said slide member is pushed by said spring member.

21. The surgical instrument as claimed in claim 20, wherein said shoulder means includes a protrusion which extends into said groove to prevent rotation of said cutting member.

22. The surgical instrument as claimed in claim 17, further comprising a remote tripping device cooperating with said spring arm providing remote movement thereof.

23. A method for creating an incision in tissue comprising the steps of:

providing a surgical instrument including:

a tubular body having a distal portion and a proximal portion;

an elongated tubular cutting member having a cutting edge, said cutting member being constructed and arranged with respect to said tubular body so as to be longitudinally received within said tubular body for guided longitudinal reciprocal movement therein between a cutting position wherein said cutting edge projects from said distal portion and a non-cutting position wherein said cutting edge is retracted within the tubular body;

means for selectively urging said cutting member and thus said cutting edge from the non-cutting position to the cutting position; and a vacuum source coupled to at least one of said tubular body and said cutting member, said vacuum source being constructed and arranged with respect to one of said tubular body and said cutting member so as to generate a vacuum therein;

directing the distal portion of the instrument to the tissue so that a blunt end of the distal portion is in contact with a portion of the tissue to be cut;

activating said vacuum source so that a vacuum is created at the distal portion of the instrument so as to hold the portion of the tissue to be cut;

actuating said urging member so as to move said cutting member from the non-cutting position to the cutting position, thereby causing said cutting edge to project from said blunt end and cut the tissue; and removing the distal portion of the instrument and the cut portion of the targeted tissue from remaining tissue.

* * * * *